| United States Patent [19] | [11] Patent Number: 4,956,231 |
|---|---|
| Cavezzan et al. | [45] Date of Patent: Sep. 11, 1990 |

[54] LAMINATED SHAPED ARTICLE/SILICONE TRANSFER ADHESIVE

[75] Inventors: Jacques Cavezzan, Villeurbanne; Jean-Louis Di Martino, Saint-Jean de Bournay, both of France

[73] Assignee: Rhone-Poulenc Chimie, Courbevoie, France

[21] Appl. No.: 231,441

[22] Filed: Aug. 12, 1988

[30] Foreign Application Priority Data

Aug. 14, 1987 [FR] France ............................... 87 11697

[51] Int. Cl.⁵ ........................... C09J 7/02; B32B 9/04; B32B 9/06
[52] U.S. Cl. ..................................... 428/343; 428/40; 428/352; 428/355; 428/447; 428/448; 428/450; 428/452; 428/914; 528/15
[58] Field of Search ............... 428/448, 450, 452, 914, 428/913, 447, 40, 355, 343, 352; 424/448

[56] References Cited

U.S. PATENT DOCUMENTS

| 3,159,662 | 12/1964 | Ashby | 528/15 |
|---|---|---|---|
| 3,715,334 | 2/1973 | Karstedt | 528/15 |
| 3,775,452 | 11/1973 | Karstedt | 556/10 |
| 3,814,730 | 6/1974 | Karstedt | 528/15 |
| 4,460,371 | 7/1984 | Abber | 424/448 |
| 4,640,939 | 2/1987 | Caveggan et al. | 428/447 X |

FOREIGN PATENT DOCUMENTS

| 0033193 | 5/1981 | European Pat. Off. | 428/447 |
|---|---|---|---|
| 0180377 | 7/1986 | European Pat. Off. | . |
| 0252858 | 1/1988 | European Pat. Off. | 428/447 |
| 2073765A | 10/1981 | United Kingdom | 428/447 |

*Primary Examiner*—Thomas J. Herbert
*Attorney, Agent, or Firm*—Burns, Doane, Swecker & Mathis

[57] ABSTRACT

Peelable, laminated shaped articles well adapted as transfer adhesives useful, e.g., for the restoration of works of art, include (i) a flexible first substrate having a nonstick polyaddition cyclotrisoloxane/organopolysiloxane composition crosslinked from an organic solvent solution on at least one face surface thereof, (ii) a precured adhesive layer adhered onto the at least one nonstick silicone layer, wherein the adhesive comprises an organopolysiloxane devoid or organic peroxide and constituting the intercondensation product of an MQ resin with a phenylated resin having silanol end groups, and (iii) a second substrate adhered to the opposite face surface of the precured adhesive layer.

10 Claims, No Drawings

LAMINATED SHAPED ARTICLE/SILICONE TRANSFER ADHESIVE

BACKGROUND OF THE INVENTION

1. Field of the Invention:

The present invention relates to polysiloxane compositions which are particularly suitable for the production of peelable coatings, and very especially suitable for transfer adhesives in which the adhesive layer and the nonstick layer are both silicone formulations.

2. Description of the Prior Art:

Nonstick coatings can be used in all cases where it is necessary to produce a surface or a material which is relatively nonadhesive to other materials to which it would normally adhere. Nonstick silicone compositions are widely employed for papers as coatings which are removed from contact adhesives, for labels, decorative laminates, adhesive transfer tapes, and the like. Nonstick silicone coatings for paper, polyethylene, Mylar and other substrates of such type can also be used as nontacky surfaces for applications in the handling of food products and in industrial packaging. These coatings are normally in a solvent-free state, in the form of a solution in a solvent, or in the form of an aqueous emulsion.

When labels are coated with an adhesive, it is desirable that the paper backing be easily removed from the label when it is about to be used, without the adhesive nature of the label being altered by its separation from the substrate on which it has been stored. The same principle applies to certain types of adhesive tapes in roll form. The tape has to unwind easily while retaining its adhesive properties. This can be achieved by covering the nonadhesive side of the tape with a peelable nonstick silicone composition which will be placed in contact with the adhesive when the roll of tape is manufactured.

Nonstick coatings can be employed in combination with silicone-based adhesives to form a system of transfer adhesives. An adhesive of this type can have many applications such as, for example, the restoration of works of art, as described in detail in French Patent No. FR-A-2,478,657 and European Patent No. EP-A-33,193. In an adhesive of this type, a first substrate, normally consisting of any type of nonporous film or of glazed paper, and preferably supercalendered kraft paper, is covered with a nonstick silicone coating, which can be removed from a reactive silicone-based contact adhesive. These two compositions will be described hereinbelow. The nonstick coating is cured on the first substrate by well known means, and normally by heat. The silicone-based contact adhesive is then applied onto the nonstick coating and is cured in place, such that the first substrate now bears two coatings, namely, the nonstick silicone coating and the silicone adhesive.

The first substrate bearing the twin coating is then applied onto a second substrate which is suitable for reinforcement and for the restoration of the work of art, such as to define a laminate. When this stage of forming a laminate has been completed, a transfer adhesive system is available, and this can be employed to reinforce the work of art whenever this may be desired in the future. The restoration is carried out by separating the first substrate and its nonstick coating from the second substrate, which retains the silicone-based contact adhesive, since the reactive adhesive adheres much more strongly to the second substrate than to the nonstick coating with which it was in contact. The silicone adhesive has thus been transferred from the substrate bearing the nonstick coating and there results a second reinforcing substrate on the work of art to constitute a laminate.

A transfer adhesive system of this type is quite obviously not limited to the restoration of paintings, but can be employed whenever it is desirable to apply a completely cured contact adhesive to virtually any sort of substrate. Once the adhesive has been transferred, it is immediately ready for use if moderate pressures are applied.

These transfer adhesive systems based on silicones have the further advantage of remaining flexible over a wide temperature range. This flexibility is not present in organic adhesives such as acrylic substances or epoxy resins, which form inefficient adhesives when applied to a substrate which normally is subjected to relatively high or low temperatures. For example, a transfer adhesive system based on silicone having a high content of phenyl groups will be particularly useful when it is desired to apply an adhesive to a motor. Organic adhesives will flake off, will split or will not satisfactorily adhere to a substrate of this type. However, the silicone adhesive can be deposited onto its transfer substrate bearing a nonstick coating and may be cured thereon, after which it can be later transferred onto the hot section of the motor, which will retain the adhesive. A silicone-based contact adhesive can withstand the temperatures, normally high, to which a motor may be subjected. A label or another laminate can subsequently be applied onto this adhesive.

In a transfer adhesive of this type, the technical problem is extremely difficult to solve.

The nonstick coating and the adhesive must, in fact, adhere sufficiently to each other to ensure the coherence of the laminate. This adhesiveness must obviously remain moderate such that the adhesive may be easily and completely transferred when the laminate is employed. In addition, this adhesive, once separated from the nonstick silicone coating, must adhere sufficiently to the substrate onto which it is transferred.

This substrate may be of any nature and may in particular be a silicone elastomer containing a medication in the case of the transdermal administration of such medication. The silicone elastomer which is thus adhesive-treated must exhibit good adhesion to the patient's skin.

SUMMARY OF THE INVENTION

Accordingly, a major object of the present invention is the provision of an improved flexible laminate comprising a specific nonstick silicone composition and specific silicone adhesive.

Surprisingly and unexpectedly vis-a-vis the teachings of FR-A-2,478,657 and EP-A-33,193 discussed above, it has now been shown that:

(1) the nonstick organopolysiloxane composition must be employed in solution in an organic solvent, must be free from MQ resin, and must contain specific ingredients; and (2) the phenylated silicone adhesive must not contain any organic peroxides.

Briefly, the present invention features a flexible laminated article comprising:

(i) a first substrate having on at least one face surface thereof a silicone nonstick layer produced by the crosslinking of an organopolysiloxane composition which comprises:
(a) at least one organopolysiloxane comprising at least two SiVi groups per molecule (Vi=vinyl),
(b) at least one organohydropolysiloxane containing at least three SiH groups per molecule,
(c) a catalytically effective amount of a hydrosilylation catalyst which is a compound of a metal of the platinum group, characterized in that from 0.5 to 60%, preferably from 1.5 to 20% of the number of SiVi groups in the composition are contributed by a vinylated cyclotrisiloxane of the formula:

$$R(CH_2=CH)SiO_3 \quad (1)$$

in which R is a $C_1$-$C_4$ alkyl radical, a phenyl radical or a 3,3,3-trifluoropropyl radical, with R preferably being a methyl radical, and
(d) an organic solvent constituting 30 to 99% by weight of the total weight of the solution;
(ii) a layer of adhesive applied onto the nonstick layer, the adhesive being an organopolysiloxane which is free from organic peroxide and which is the product of intercondensation of an MQ resin and of a polyalkylphenylsiloxane resin; and
(iii) a second substrate applied onto the adhesive.

DETAILED DESCRIPTION OF THE PREFERRED EMBODIMENTS OF THE INVENTION

More particularly according to the present invention, all percentages and parts given herein are by weight, unless otherwise stated.

The nonstick organopolysiloxane composition is described in detail in published French Patent Application No. 86/09,311, filed June 24, 1986.

The base organopolysiloxanes (a) are characteristically diorganopolysiloxanes of the formula:

$$R_2R'SiO(SiR_2O)_n(SiRR'O)_mSiR_2R' \quad (2)$$

in which n and m are integers which may be zero separately and whose sum has a value such that the organopolysiloxane has a viscosity of at least 20 mPa.s and not more than 30,000,000 mPa.s at 25° C., the radicals R, which may be identical or different, are as defined in formula (1) above and R' is R or a vinyl radical, with the proviso that when m=0, R' is a vinyl radical.

The organopolysiloxanes (a) may also preferably comprise the diorganocyclosiloxanes of the formula:

$$R(CH_2=CH)SiO_p \quad (3)$$

in which R is as defined above and p is an integer ranging from 4 to 10 inclusive.

The organopolysiloxanes (a) of the formulae (2) and (3) well known to this art and are particularly described in U.S. Pat. Nos. 3,220,972, 3,344,111 and 3,436,366, these patents also describing the organohydropolysiloxanes (b).

At least 60 mol % of the radicals R are preferably methyl radicals and, still more preferably, all the radicals R are methyl radicals.

The organohydropolysiloxane (b) may be linear, cyclic or branched.

The substantially linear or branched organohydropolysiloxane (b) has recurring units of the average general formula:

$$R_xH_ySiO_{\frac{4-x-y}{2}} \quad (4)$$

in which the radicals R, which may be identical or different, are as defined above, with the proviso that certain radicals R may be vinyl radicals. At least 80% of the radicals R are methyl radicals.

The symbol x denotes any number from 1 to 1.99, the symbol y denotes any number from 0.1 to 1, with the sum x+y ranging from 1.7 to 2.6. Methylhydropolysiloxanes are preferably employed as the organohydropolysiloxanes (b).

The organohydropolysiloxanes (b) are commercially available and, in addition, various processes for the preparation thereof are well known to this art. One of the most widely employed methods consists, in a first stage, of cohydrolyzing suitable mixtures of chlorosilanes selected from among those of the formulae: $R_3SiCl$, $R_2SiCl_2$, $RSiCl_3$, $SiCl_4$, $HR_2SiCl$, $HRSiCl_2$ and $HSiCl_3$. By "suitable mixtures" are intended mixtures, each of which contains, per silicon atom, a number of radicals R and a number of hydrogen atoms coinciding with the values denoted by the symbols x and y in the average general formula, respectively, with the sum of these numbers also having to coincide with the permitted values for the sum x+y.

In a second stage, the cohydrolysates are heated to a temperature ranging from 80° to 220° C., preferably in the presence of acidic agents such as sulfuric acid or earths activated with an acid. A rearrangement of the siloxane bonds and condensation of the SiOH groups take place during this heating. These conversions produce the organohydropolysiloxane polymers (b), which thus contain linear, cyclic or branched structures, depending on the initial chlorosilane mixtures.

The constituents (a) and (b) are generally present in the composition in such quantity that the numerical ratio of the SiH groups to the SiVi groups ranges from 0.5 to 5, preferably from 0.6 to 2.5.

In the coating applications and more particularly in the applications for imparting nonstick characteristics to paper, from 0.1 to 50 parts by weight of polymer (b) may be employed per 100 parts by weight of polymer (a).

As catalyst (c), there may be employed compounds of a platinum group metal, in particular their salts and complexes, especially the platinum-olefin complexes as described in U.S. Pat. Nos. 3,159,601 and 3,159,662, the products of reaction of platinum derivatives with alcohols, aldehydes and ethers described in U.S. Pat. No. 3,220,972, the platinum-vinylsiloxane catalysts described in French Patent No. FR-A-1,480,409, and the complexes described in U.S. Pat. Nos. 3,715,334, 3,775,452 and 3,814,730, as well as a rhodium catalyst as described in U.S. Pat. Nos. 3,296,291 and 3,928,629.

The preferred platinum group metals are platinum and rhodium; ruthenium, although less active, but less costly, can also be employed.

From 5 to 200 ppm of catalyst, calculated as the weight of metal relative to the weight of the polysiloxanes containing SiVi and SiH, are typically employed.

The nonadhesive compositions according to the invention must be in solution in a volatile organic solvent selected, for example, from among the alkanes, petroleum fractions containing paraffinic compounds, toluene, heptane, xylene, isopropanol, methyl isobutyl ketone, tetrahydrofuran, chlorobenzene, chloroform, 1,1,1-trichloroethane, and derivatives of monoethylene glycol and of methylene glycol.

Preferably, the solvent constitutes from 50 to 99% by weight of the solution at the time of use.

After evaporation of the solvent, the nonstick composition cures at room temperature or, more rapidly, upon heating thereof. These solutions can therefore be used as nonstick coating compositions for flexible substrates made of metal, paper, plastic, cardboard, and the like, which can define the first substrate of the laminate according to the invention To render the first substrate nonsticky, a quantity of composition according to the invention, generally from 0.1 to 10 g, is applied per m² of surface to be coated and the composition is crosslinked thermally.

The compositions may be applied with the aid of the devices employed on industrial paper-coating machines such as the "multipoint" gravure roll, or the system known as "Reverse Roll". Once deposited onto the substrate, the compositions are cured by the input of energy, at least a part of which may be provided by UV radiation, in a few seconds, by passing same under a UV light, and in tunnel ovens heated to about 60°–200° C.; the residence time in these ovens generally varies from 2 to 30 seconds. For a given oven length, it is a function of the speed at which the coated substrates travel (this speed can exceed 200 meters per minute).

The quantities of compositions deposited onto the substrates can vary and in most cases range from 0.1 to 10 g/m² of treated surface. These quantities depend on the nature of the substrates and on the desired nonstick properties. In most cases they range from 0.5 to 1.5 g/m² for nonporous substrates.

The compounds of formula (1) are well known to this art, and processes for their preparation are described in particular in U.S. Pat. Nos. 3,607,898, 3,763,212 and 3,989,733 and in Japanese Published Patent Application Kokai No. 74/124,067, incorporated herein by reference. Trimethyltrivinylcyclotrisiloxane is preferably employed.

The materials of formula (1) produce coatings which are harder, although sufficiently flexible, and this greatly facilitates automatic machine cutting of flexible composites, especially papers, without modification of the nonstick property.

As regards the phenylated adhesive, another subject of the present invention, this generally results from the intercondensation of a mixture of a polyorganosiloxane resin and at least one polyalkylarylsiloxane resin. A particularly useful adhesive comprises 100 parts by weight of a polyalkylphenylsiloxane resin having silanol end groups and a viscosity of from 1 to 200 million centipoises at 25° C. and an organophenylsiloxy unit content of from 5 to 40 mole percent of the moles of recurring units constituting the resin. A polydimethyldiphenylsiloxane resin with silanol end groups which has a diphenylsiloxy group content of from 5 to 25 mole percent and a viscosity of from 20 to $80 \times 10^{+6}$ mPa.s at 25° C. is particularly preferred. This resin is combined with from 50 to 200 parts by weight of an MQ silicone resin such as described, for example, in U.S. Pat. No. 2,676,182, with a ratio of M to Q of from 0.5 to 1.0.

For example, 100 parts of the above resin may be combined with 100 to 150 parts of MQ resin, wherein M denotes $(CH_3)_3SiO_{1/2}$ and Q denotes $(SiO_2)$.

This intercondensation, performed before the coating with the adhesive, is preferably carried out by heating the mixture of the resin and of the MQ resin to 80°–120° C. in the presence of basic catalysts such as NaOH, KOH or potassium silanolate.

Suitable phenylated adhesives are described, for example, in U.S. Pat. No. 2,857,356.

The production of the flexible laminate containing a silicone-based transfer adhesive comprises the stages of deposition and of curing the nonstick coating on a first substrate, which will normally be made of paper or an organic polymer film. The paper may be in the form of sheets or in roll form, and the like. At least one of the face surfaces of the paper or of another substrate must be coated. However, if both sides are coated, the doubly coated paper may be wound like a tape.

A coating of silicone-based contact adhesive is then deposited onto the nonstick coating, and this is then precured or precrosslinked using well known processes onto the nonstick coating, generally by heating to 60°–150° C. with removal of the solvent.

When the silicone adhesive is cured onto the nonstick coating, it is ready for use, or it can be stored for subsequent use.

The first substrate is now doubly coated with the nonstick coating and the adhesive film. The doubly coated substrate can then be applied onto a second substrate which is to be rendered adhesive. This second substrate may be a silicone elastomer. The first substrate bearing the nonstick coating is then separated or removed from the second substrate, and this results in the film of adhesive being transferred onto the second substrate. The second substrate has now become adhesive and it may be applied onto a third substrate, which may be, for example, a patient's skin in the case where the second substrate is a silicone elastomer (transdermal administration of a medication). In this latter case, the silicone elastomer containing the medication originates from the crosslinking of an organopolysiloxane composition adapted for the release of the medication towards the patient's skin. Such organopolysiloxane compositions are known. They are described, for example, in U.S. Pat. No. 4,331,651.

It will be appreciated, obviously, that the second substrate may consist of the component which it is desired to make adhesive immediately, or of a surface bearing a nonstick coating such as the reverse of a substrate tape for an adhesive.

In order to further illustrate the present invention and the advantages thereof, the following specific examples are given, it being understood that same are intended only as illustrative and in nowise limitative.

EXAMPLE 1:

1. Preparation of the nonstick silicone composition:

The following mixture was homogenized:
(i) 300 parts of a polyvinylmethyldimethylsiloxane resin containing vinyl units in the polymer chain and a trimethylsiloxyl end group, containing approximately 0.07% by weight of vinyl groups and exhibiting a viscosity of approximately $20 \times 10^6$ mPa.s at 25° C.;
(ii) 7 parts of 1,3,5,7-tetramethyl-1,3,5,7-tetravinylcyclotetrasiloxane (D$_4$Vi);
(iii) 8 parts of a hydromethyldimethylpolysiloxane copolymer containing methylhydrosiloxyl and dimethylsiloxyl recurring units and a trimethylsiloxyl end group, containing approximately 1% by weight of hydrogen atoms bonded to silicon and with a viscosity of approximately 45 mPa.s at 25° C.; and (iv) 685 parts of toluene.

To this bath were added:

(v) 1 part of trimethyltrivinylcyclotrisiloxane (D₃Vi); and (vi) 60 ppm of platinum ($3 \times 10^{-4}$ g-at. of Pt/kg of composition) in the form of a platinum complex prepared from chloroplatinic acid and 1,3-divinyl-1,1,3,3-tetramethyldisiloxane, as described in Example 3 of U.S. Pat. No. 3,814,730.

The mixture was stirred vigorously for a few minutes at ambient temperature and this mixture was then deposited (approximately from 1 to 3 g/m²) onto a Terphane ® polyester film by means of a coating bar and the silicone composition was cured for 10 seconds in a forced air circulation oven set at 120° C.

2. Preparation of the silicone adhesive:

MQ resin: this resin comprised recurring units M:(CH₃)₃SiO₀.₅ and Q:SiO₂, distributed in an M/Q molar ratio of 0.6; it contained 3.4% of OH radicals, and its Mn was on the order of 5000.

Phenylated resin: this resin was a polydimethyldiphenylsiloxane with silanol end groups, with a viscosity of 30 million mPa.s at 25° C. and with a diphenylsiloxy unit content of 7% by weight.

Preparation of the adhesive: a mixture of 21.7 parts of resin, 33.3 parts of MQ resin and xylene was homogenized.

The mixture was heated to 90° C. for 2 hours in the presence of 40 parts of potassium hydroxide per million parts of resin +MQ resin, and an adhesive having a solids content of 55%, exhibiting a viscosity of 60,000 mPa.s at 25° C., was obtained.

The silicone adhesive was deposited onto the Terphane film coated with the silicone nonstick, using a doctor blade, onto the nonstick layer, at a rate of 60 g of adhesive per m².

The xylene in the adhesive was evaporated off by heating the tape for 2 minutes at 100° C.

The adhesive-coated Terphane film was bonded adhesively onto a polyaddition silicone elastomer tape marketed by Rhone-Poulenc under the trademark RTV 141 ®.

The entire laminate was subjected to a pressure of 4.5 mPa at ambient temperature.

The laminate obtained was maintained at ambient temperature for 48 hours and the parting forces F were measured in g/cm according to European standard AFERA 4001.

A complete and faultless transfer of the adhesive onto the silicone elastomer was obtained, reflecting a parting force of from 100 to 150 g/cm.

COMPARATIVE EXAMPLE 2:

The procedure was exactly as in Example 1, except that the nonstick coating comprised 3.5 parts of MQ resin employed for the adhesive, per 100 parts of solids content. A slowing of the rate of polymerization of the nonstick layer was observed, and the transfer of adhesive was of poor quality.

COMPARATIVE EXAMPLE 3:

The procedure was exactly as in Example 1, except that the adhesive comprised 2 parts of 2,4-dichlorobenzoyl peroxide per 100 parts of adhesive solids.

The transfer of adhesive was nonexistent after parting.

COMPARATIVE EXAMPLE 4:

The procedure was exactly as in Comparative Example 2, except that the adhesive additionally contained peroxide under the same conditions as in Comparative Example 3.

The transfer of the adhesive onto the silicone elastomer after parting was unsuccessful.

EXAMPLE 5:

The procedure was exactly the same as in Example 1, except that the nonstick composition to be catalyzed had the following composition:

(i) 350 parts of the vinylated resin employed in Example 1;

(ii) 150 parts of a dimethylpolysiloxane oil blocked with dimethylvinylsiloxy units at each of its polymer ends, with a viscosity of 1000 mPa.s at 25° C., and with a weight content of 0.3% of vinyl radicals bonded to the silicon atoms;

(iii) 7 parts of D₄Vi;

(iv) 8 parts of the same hydromethyldimethylpolysiloxane copolymer employed in Example 1; and (v) 485 parts of toluene.

The adhesive-coated Terphane film was bonded adhesively onto a paper coated with polyethylene instead of the silicone elastomer.

A complete and faultless transfer of the adhesive was obtained, reflecting a parting force of 170 g/cm.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A peelable, laminated shaped article comprising (i) a flexible first substrate having a crosslinked nonstick silicone layer on at least one face surface thereof, which nonstick silicone layer comprises an organopolysiloxane composition crosslinked from an organic solvent solution thereof and said organopolysiloxane composition being free from MQ resin and (a) at least one oganopolysiloxane comprising at least two SiVi groups per molecule, and (b) at least one organohydropolysiloxane comprising at least three SiH groups per molecule, with from 0.5 to 60% of the number SiVi groups in the composition being provided by a vinylated cyclotrisiloxane of the formula:

$$R(CH_2=CH)SiO_3 \qquad (I)$$

in which R is a $C_1$–$C_4$ alkyl radical, a phenyl radical or a 3,3,3-trifluoropropyl radical, and (ii) a precured adhesive layer adhered onto at least one nonstick silicone layer, said adhesive comprising an organopolysiloxane devoid of organic peroxide and constituting the intercondensation product of an MQ resin with a polyalkylphenylsiloxane resin.

2. The laminated shaped article as defined by claim 1, wherein from 1.5 to 20% of the number of SiVi groups in the organopolysiloxane composition are provided by said vinylated cyclotrisiloxane of the formula (1).

3. The laminated shaped article as defined by claim 1, said at least one organopolysiloxane (a) comprising a diorganopolysiloxane.

4. The laminated shaped article as defined by claim 1, said organopolysiloxane composition (i) comprising from 0.1 to 50 parts by weight of said at least one organohydropolysiloxane (b) per 100 parts by weight of said at least one organopolysiloxane (a).

5. The laminated shaped article as defined by claim 1, said flexible first substrate (i) comprising paper, metal, plastic or cardboard.

6. The laminated shaped article as defined by claim 1, said organopolysiloxane composition further including a catalytically effective amount of platinum group metal hydrosilylation catalyst.

7. The laminated shaped article as defined by claim 6, the organic solvent originally constituting from 50 to 99% by weight of the total weight of the solution of said organopolysiloxane composition.

8. The laminated shaped article as defined by claim 1, further comprising (iii) a second substrate adhered to the opposite face surface of said precured adhesive layer.

9. The laminated shaped article as defined by claim 8, said second substrate (iii) comprising a silicone elastomer.

10. The laminated shaped article as defined by claim 9, said silicone elastomer comprising a medicament.

* * * * *